(12) United States Patent
Kawakubo et al.

(10) Patent No.: US 8,708,534 B2
(45) Date of Patent: *Apr. 29, 2014

(54) LIGHT-EMITTING DEVICE

(75) Inventors: Kiyoshi Kawakubo, Kanuma (JP); Wataru Suzuki, Kanuma (JP); Toshiyuki Sadohara, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/717,636

(22) Filed: Mar. 4, 2010

(65) Prior Publication Data

US 2010/0226132 A1 Sep. 9, 2010

(30) Foreign Application Priority Data

Mar. 5, 2009 (JP) .................................. 2009-51428

(51) Int. Cl.
*F21V 3/00* (2006.01)

(52) U.S. Cl.
USPC ................. 362/311.02; 362/311.04; 362/573; 433/29

(58) Field of Classification Search
USPC ............... 362/311.02, 311.04, 804, 572, 573; 433/29
See application file for complete search history.

(56) References Cited

U.S. PATENT DOCUMENTS

| | | | | |
|---|---|---|---|---|
| 300,524 A | * | 6/1884 | Starr | 362/139 |
| 1,617,417 A | * | 2/1927 | Ray | 112/75 |
| 1,793,463 A | * | 2/1931 | Cameron | 362/399 |
| 2,176,620 A | * | 10/1939 | Beam | 433/31 |
| 3,955,124 A | * | 5/1976 | Jones | 361/782 |
| 5,636,984 A | * | 6/1997 | Gomes | 433/30 |
| 6,331,111 B1 | | 12/2001 | Cao | |
| 6,837,606 B2 | * | 1/2005 | Baillie-Hamilton | 362/558 |
| 7,066,734 B1 | * | 6/2006 | Cooper | 433/31 |
| 7,273,369 B2 | * | 9/2007 | Rosenblood et al. | 433/29 |
| 7,294,364 B2 | * | 11/2007 | Cao | 427/508 |
| 7,618,154 B2 | * | 11/2009 | Rosiello | 362/202 |
| 7,726,863 B2 | * | 6/2010 | Brandstaetter et al. | 362/572 |
| 8,029,439 B2 | * | 10/2011 | Todd et al. | 600/178 |
| 2006/0044823 A1 | | 3/2006 | Wong et al. | |
| 2006/0173245 A1 | * | 8/2006 | Todd et al. | 600/178 |
| 2009/0017416 A1 | | 1/2009 | Nguyen et al. | |
| 2010/0226133 A1 | * | 9/2010 | Kawakubo et al. | 362/311.02 |

FOREIGN PATENT DOCUMENTS

| | | |
|---|---|---|
| FR | 2 725 080 A1 | 3/2006 |
| JP | 62-29184 A | 2/1987 |
| JP | 10137263 A | 5/1998 |
| JP | 2004-321422 A | 11/2004 |
| JP | 2007-227422 A | 9/2007 |

* cited by examiner

*Primary Examiner* — John A Ward
(74) *Attorney, Agent, or Firm* — Jason D. Voight

(57) ABSTRACT

The light-emitting device 1 has a translucent cover 10 having a cylindrical shape and a flat light-projecting surface 11 facing to the light-emitting part of an LED 20. The LED 20 is arranged in close proximity with the flat light-projecting surface 11 in the translucent cover 10 to achieve efficient introduction of light from the LED 20 into a light-receiving surface of optical fibers.

6 Claims, 5 Drawing Sheets

LIGHT-EMITTING DEVICE

FIELD OF ART

The present invention relates to a light-emitting device which may be used as a light source in a lighting device mounted on a dental handpiece. In particular, the present invention relates to a light-emitting device utilizing a light-emitting diode (LED).

BACKGROUND ART

LEDs have recently been attracting attention and widely used as a light source in a lighting device mounted on a dental handpiece for their lower electric power consumption and longer service life compared to conventional halogen lamps. JP-10-137263-A discloses a light-emitting device which includes an LED enclosed in a translucent cover, and electrode terminals electrically connected to and linearly extending from the LED, and is in a compact size as a whole suitable for installation in a dental handpiece. The translucent cover enclosing the LED is in the form of a bullet, out of which the two linear terminals (anode and cathode terminals) connected to the LED extend. The light-emitting device is installed in a dental handpiece with the two linear terminals being connected to the connecting terminals of a lighting device arranged in a coupling connecting a handpiece body and a hose. In the installed state, the light-emitting device is arranged facing to the light-receiving surface of the optical fibers disposed in the handpiece body to introduce light emitted from the LED into the optical fibers.

However, in such a conventional light-emitting device, the LED is inevitably arranged apart from the light-projecting surface of the translucent cover facing to the LED, due to the bullet shape of the cover and the semispherical shape of the light-projecting surface. Accordingly, the distance from the light-emitting part of the LED to the semispherical light-projecting surface is added to the distance between the light-emitting part of the LED and the light-receiving surface of the optical fibers. The light emitted from the LED is scattered between the light-emitting part of the LED and the semispherical light-projecting surface, and is not efficiently introduced into the light-receiving surface of the optical fibers. This reduces the amount of light entering the optical fibers to lower the intensity of illumination (brightness) and causes color shading.

SUMMARY OF THE INVENTION

It is therefore an object of the present invention to provide a light-emitting device in which the light-emitting part of an LED is arranged in as close proximity to the light-receiving surface of optical fibers as possible for efficient introduction of light from the LED into the light-receiving surface to increase the amount of light entering the optical fibers, to improve the brightness of the lighting device, to eliminate or minimize color shading, and to improve the quality of the lighting device.

According to the present invention, there is provided a light-emitting device comprising:
 a translucent cover,
 a light-emitting diode (LED) enclosed in said translucent cover, and
 electrode means electrically connected to said LED,
 wherein said light-emitting device is in such a compact size as to be disposed in a dental handpiece, characterized in that said translucent cover has a generally cylindrical shape and a flat light-projecting surface facing to a light-emitting part of said LED.

The light-emitting device according to the present invention, having the structure mentioned above, allows arrangement of the light-emitting part of the LED in as close proximity to the light-receiving surface of optical fibers as possible when the light-emitting device is installed in a lighting device having optical fibers. Thus, the light from the LED is efficiently introduced into the light-receiving surface of the optical fibers to maximize the amount of light entering the optical fibers. The increased amount of light improves the brightness of the lighting device and eliminates or minimizes color shading, to thereby improve the quality of the lighting device.

PREFERRED EMBODIMENTS OF THE INVENTION

The present invention will now be explained in detail with reference to an embodiment taken in conjunction with the attached drawings.

Figure 1:
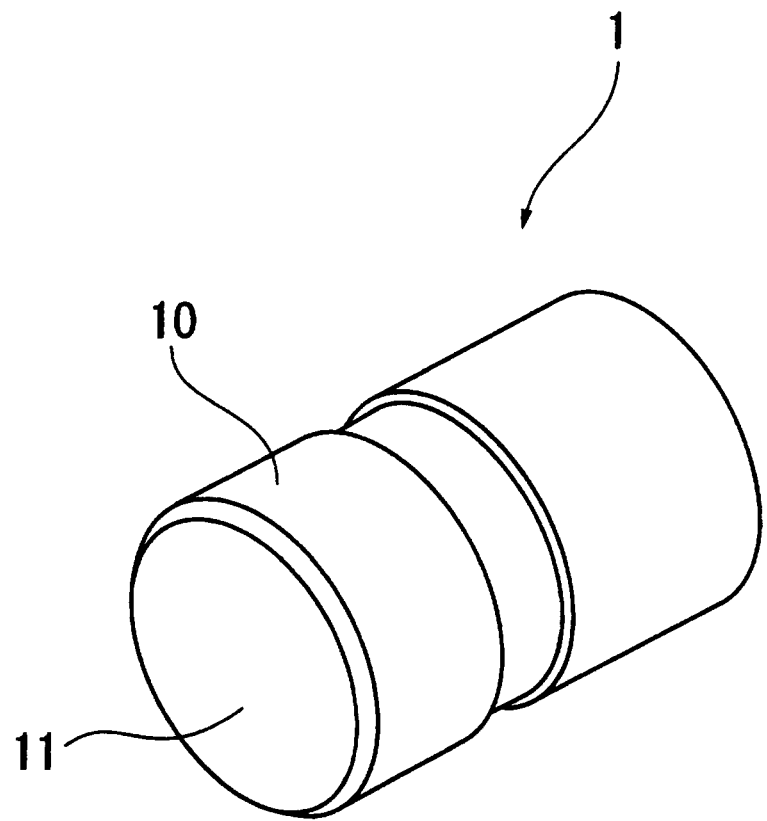
FIG. 1 is a perspective view of an embodiment of the light-emitting device according to the present invention.
Figure 2:
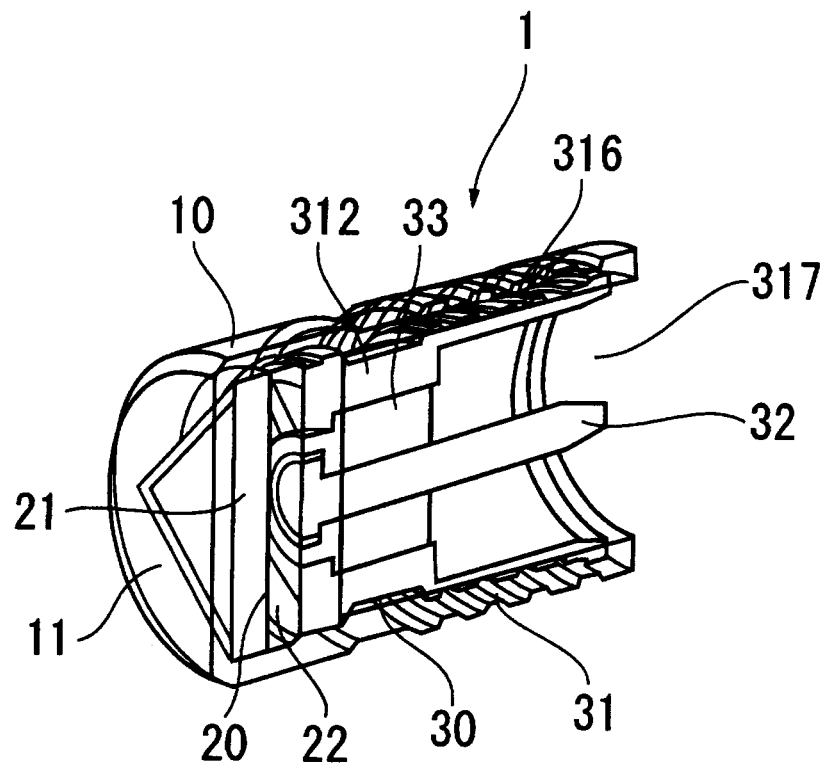
FIG. 2 is a perspective view of the device of FIG. 1 in section, illustrating the structure of the device.
Figure 3:
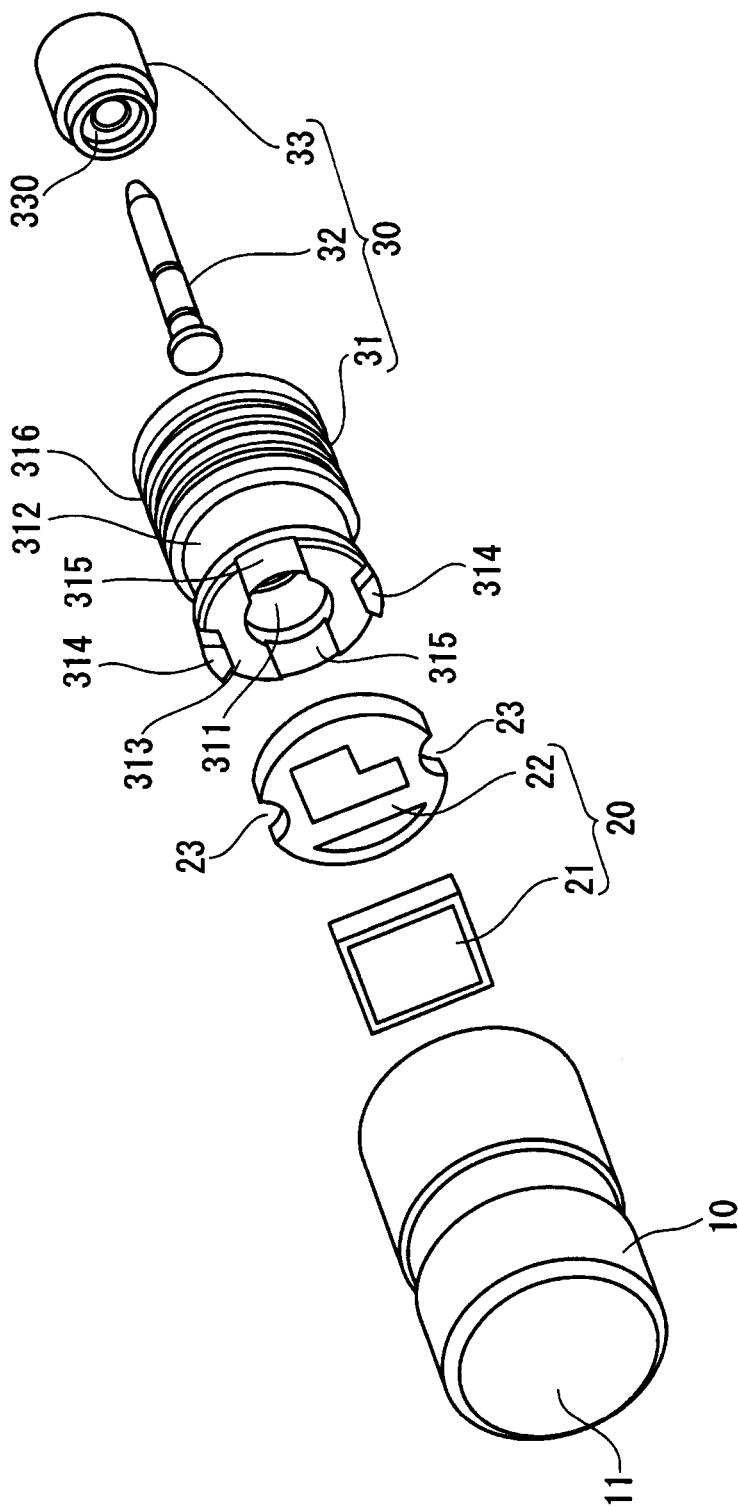
FIG. 3 is an exploded perspective view of the device of FIG. 1.

FIGS. 1 to 5 show an embodiment of the light-emitting device according to the present invention. Referring to FIGS. 1 and 3, the light-emitting device 1 has translucent cover 10, LED 20 enclosed in the cover 10, and electrode means 30 enclosed in the cover 10 and electrically connected to and extending from the LED 20. The light-emitting device 1 as a whole is of such a compact size as to be installed in a dental handpiece.

Figure 4:
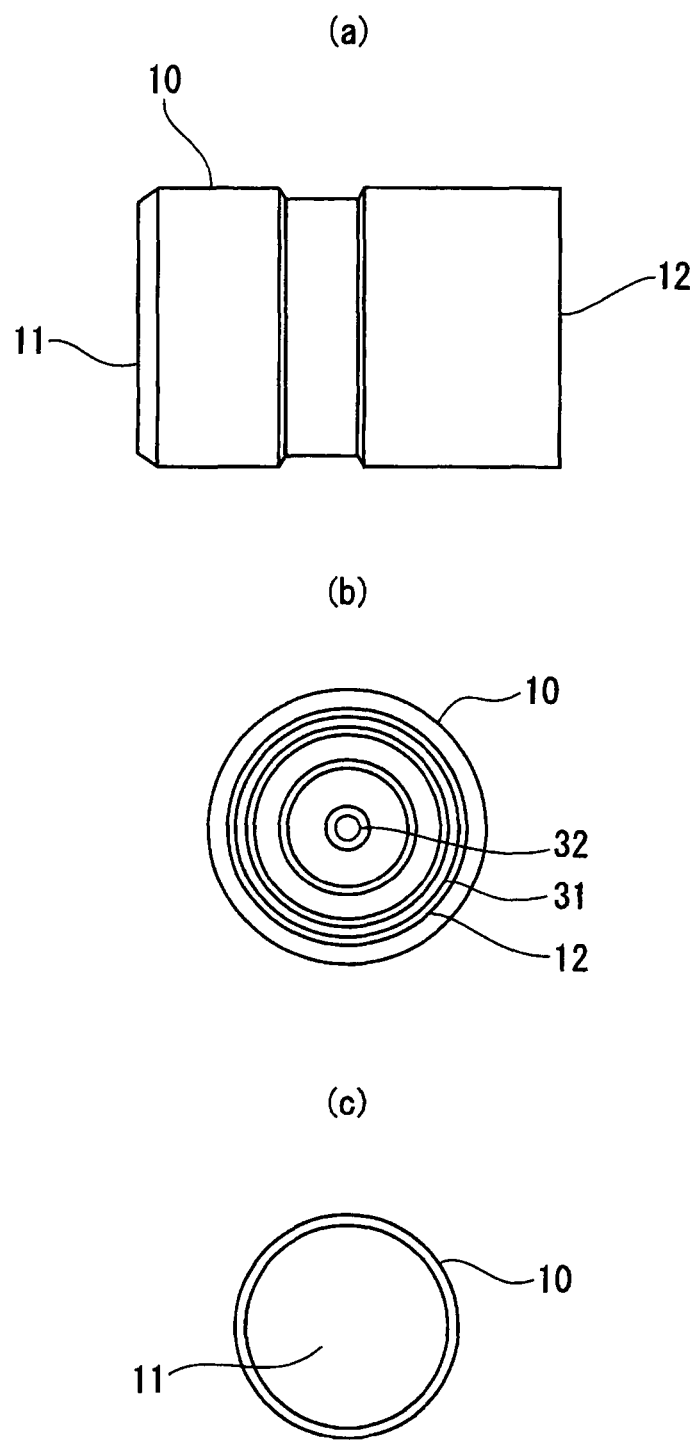
FIG. 4($a$) is a side view, FIG. 4($b$) is a bottom view, and FIG. 4($c$) is a plan view of the device of FIG. 1.
Figure 5:
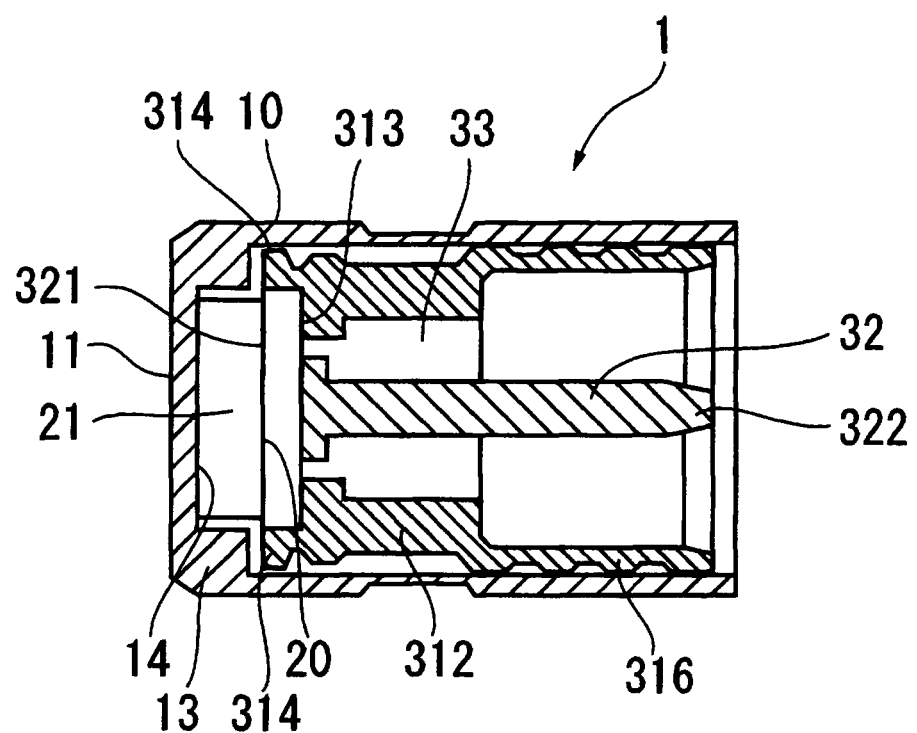
FIG. 5 is a longitudinal sectional view of the device of FIG. 1.

The translucent cover 10 is a generally cylindrical member made of a transparent synthetic resin in its entirety, and has end face 11 at one end, which is a closed, flat, circular surface, and end opening 12 at the other end, which is a circular opening, as shown in FIG. 4. As can be seen in FIG. 5, inside the cover 10, an annular step 13 is formed along the inner circumference near the end face 11, and rectangular dent 14 is formed in the inner surface on the inside of the end face 11. The dent 14 is sized to receive the LED 20 (in particular, LED chip 21 as will be discussed later) therein, and the end face 11 to be faced to the light-emitting part of the LED 20 acts as a light-projecting surface. The dent 14 is arranged so that the cover 10 and the LED 20 received therein are positioned concentrically.

Referring to FIG. 3, the LED 20 includes LED chip (LED element) 21 and substrate 22. The LED chip 21 is a rectangular member, and is sized to be arranged in the dent 14 in the cover 10. A fluorescent material is laminated on the LED chip 21. The substrate 22 is in the form of a generally circular disk having a diameter smaller than the inner diameter of the cover 10 so as to be arranged in the cover 10, and is slightly larger than the LED chip 21. Two arcuate notches 23, 23 are formed on the periphery of the substrate 22 at diametrically opposite positions.

Referring further to FIG. 3, the electrode means 30 includes cathode terminal (negative electrode) 31, anode terminal (positive electrode) 32, and terminal support 33.

As shown in FIGS. 2 and 3, the cathode terminal 31 is a generally cylindrical member having opening 311 at one end and opening 317 at the other end. The cathode terminal 31 has larger diameter section 316, which has an outer diameter approximately the same as or slightly smaller than the inner diameter of the cover 10 and has a corrugated outer surface, and smaller diameter section 312, which is continuous to the larger diameter section 316 and has an outer diameter smaller than the outer diameter of the larger diameter section 316. Annular flange 313 is formed at the free end of the smaller diameter section 312, which projects radially inwardly for supporting the substrate 22 of the LED 20 thereon. The flange 313 has two protrusions 314, 314 projecting axially from its end face and arranged at diametrically opposite positions. Each protrusion 314 has an arcuate contour and is capable of being fitted in the notch 23 of the substrate 22 of LED 20. Two recesses 315, 315 are formed also in the end face of the flange 313 at diametrically opposite positions and at 90° angular distance from the protrusions 314, 314.

The anode terminal 32 is generally in the form of a pin having a length approximately the same as the axial length of the cathode terminal 31, and has a flange 321 projecting radially outwardly at one end and a tapered portion 322 at the other end.

The terminal support 33 is made of an electrically insulating material, and has a generally cylindrical form. The support 33 has an outer contour to fit inside the smaller diameter section 312 of the cathode terminal 31, and a stepped recess 330 in one end face, in which the flange 321 of the anode terminal 32 is fitted.

Assembly of the electrode means 30 is explained with reference to FIG. 5. First, the anode terminal 32 is inserted into the terminal support 33, and supported therein with the flange 321 being fitted in the stepped recess 330 and the tapered end 322 extending out of the free end of the support 33. The support 33, with the anode 32 supported therein, is then inserted into the cathode terminal 31, and fit in the smaller diameter section 312. The anode terminal 32, the terminal support 33, and the cathode terminal 31 are positioned concentrically, and the flange 321 of the anode terminal 32 is arranged in the opening 311 of the cathode terminal 31 via the support 33 without contacting the inner surface of the cathode terminal 31.

Next, the assembly of the light-emitting device 1 is explained with reference to FIGS. 3 and 5.

The LED chip 21 is placed in the rectangular dent 14 formed inside the cover 10 so as to be positioned concentrically with the cover 10 and to face the light-emitting part of the LED 20 to the end face 11 of the cover 10. To the electrode means 30 as assembled above, the substrate 22 of the LED 20 is attached on the flange 313 of the cathode terminal 31, with the two protrusions 314, 314 of the flange 313 being fitted in the two notches 23, 23 of the substrate 22. In this state, the flange 313 of the cathode terminal 31 is connected to the substrate 22 of the LED 20, and the flange 321 of the anode terminal 32 is connected to the substrate 22 of the LED 20. The electrode means 30 with the substrate 22 attached thereto is then inserted into the cover 10. In this way, the LED 20, the cathode terminal 31, and the anode terminal 32 are all positioned concentrically in the cover 10. In this assembly, the LED 20 is positioned close to the light-projecting surface 11 of the cover 10, and the cathode and anode terminals 31 and 32 are connected to the LED 20.

The light-emitting device 1 according to the present invention may be installed in a dental handpiece as a part of a lighting device. The connecting terminals on the side of the handpiece are in the form of a socket, which projects outwardly from the circuit board arranged in the coupling of the handpiece. The connecting terminals of the socket are configured as two concentric cylinders which are arranged via an electrically insulating material therebetween. The inner terminal has a smaller diameter so that the anode terminal 32 of the light-emitting device 1 is inserted and fitted therein. The outer terminal has a larger diameter so that the inner surface of the cathode terminal 31 of the light-emitting device 1 fits over the outer surface of the outer terminal. The connecting end of the outer terminal is divided into a plurality of flaps, which are flexed radially inwardly by means of an external force and elastically return to the initial position by removal of the external force.

The light-emitting device 1 may be connected to the circuit board in the handpiece simply by inserting the electrode means 30 of the light-emitting device 1 into the socket having the connecting terminals. That is, when the electrode means 30 of the light-emitting device 1 is inserted into the socket, the anode terminal 32 of the light-emitting device 1 is inserted into and brought into contact with the inner cylindrical terminal of the socket, whereas the cathode terminal 31 of the device 1 fits over the outer cylindrical terminal of the socket to bring the inner surface of the larger diameter portion 316 into press contact with the outer surface of the outer terminal, which elastic engagement holds the light-emitting device 1 in place in the socket. The difference in shape of the cathode terminal 31 and the anode terminal 32 clearly distinguishes the polarity of the electrode means 30, so that the light-emitting device 1 will not fail to be connected to the socket on the side of the circuit board in correct polarity. The light-emitting device 1 thus installed on the handpiece is powered through the circuit board and emits light, which is introduced into the light-receiving surface of the optical fibers.

Since the light-emitting device 1 according to the present invention has the flat light-projecting surface 11, and the LED 20 is positioned in close proximity to this surface 11, the distance between the light-emitting part of the LED chip 21 and the light-receiving surface of the optical fibers is minimized to achieve efficient introduction of light from the LED 20 into the light-receiving surface of the optical fibers. Thus the amount of light entering the optical fibers is remarkably increased compared to the conventional light-emitting device, and the brightness of the lighting device is improved and color shading is eliminated or substantially reduced.

In the electrode means 30, the cathode terminal 31 is in the form of a cylinder, while the anode terminal 32 is in the form of a pin, so that the two terminals have different shapes. This facilitates determination of the polarity of the electrode 30 to securely prevent connection of the light-emitting device 1 to the connecting terminals on the side of the circuit board in wrong polarity.

In the electrode means 30, the cathode terminal 31 is formed in a cylindrical form, and the anode terminal 32 is formed in a pin form and enclosed in the cylindrical cathode terminal 31. This arrangement makes the electrode means 30 compact compared to the conventional two linear terminals.

Since the cathode terminal 31 of the light-emitting device 1 is in the form of a cylinder, the surface area of the cathode terminal 31 is increased, which results in effective release of heat generated in the electrode means 30 through the cathode terminal 31.

Further, by assembling the cover 10, LED 20, and electrode means 30 concentrically, the processing of each part of the light-emitting device 1 and the assembly thereof are facilitated.

Incidentally, according to the embodiment of the present invention described above, the electrode means 30 is integrally assembled in the translucent cover 10 together with the LED 20. However, the flat light-projecting surface of the translucent cover may also be applied to a light-emitting device having two linear terminals extending from the translucent cover.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

DESCRIPTION OF REFERENCE NUMERALS

1 light-emitting device
10 translucent cover
11 end face (light-projecting surface)
12 opening
13 annular step
14 dent
20 LED (light-emitting diode)
21 LED chip (light-emitting element)
22 substrate
23 notch
30 electrode means
31 cathode terminal (negative electrode)
311 opening
312 smaller diameter section
313 flange
314 protrusion
315 recess
316 larger diameter section
317 opening
32 anode terminal (positive electrode)
321 flange
322 tapered end
33 terminal support
330 stepped recess

What is claimed is:

1. A light-emitting device comprising:
a translucent cover,
a light-emitting diode (LED) enclosed in said translucent cover, and
electrode means electrically connected to said LED,
wherein said light-emitting device is in such a compact size as to be disposed in a dental handpiece,
wherein said translucent cover has a generally cylindrical shape and a flat light-projecting surface facing to a light-emitting part of said LED,
wherein said translucent cover has in its inner surface a dent sized to fit a single LED therein on the inside of the light-projecting surface, said LED being positioned in said dent.

2. The light-emitting device according to claim 1, wherein said LED is positioned in the translucent cover in close proximity to said flat light-projecting surface.

3. The light-emitting device according to claim 1, wherein said electrode means comprises:
a cathode terminal generally in the form of a cylinder having an opening at each end, and
an anode terminal generally in the form of a pin capable of being arranged concentrically in said cathode terminal,
wherein said cathode terminal and said anode terminal are arranged concentrically with said LED.

4. The light-emitting device according to claim 1, wherein said dent is rectangular.

5. The light-emitting device according to claim 1, wherein said flat light-projecting surface of said translucent cover is an end face which is closed.

6. The light-emitting device according to claim 1, wherein said translucent cover and said LED are positioned concentrically.

* * * * *